United States Patent [19]

Sadler et al.

[11] Patent Number: 5,250,672
[45] Date of Patent: Oct. 5, 1993

[54] CONTRAST AGENT FOR NMR IMAGING

[75] Inventors: Peter J. Sadler, Pitstone; Charles T. Harding, Long Croft, both of England

[73] Assignee: Guerbet S.A., Villepinte, France

[21] Appl. No.: 48,091

[22] PCT Filed: Sep. 11, 1986

[86] PCT No.: PCT/GB86/00540
§ 371 Date: Jun. 30, 1987
§ 102(e) Date: Jun. 30, 1987

[87] PCT Pub. No.: WO87/01594
PCT Pub. Date: Mar. 26, 1987

[30] Foreign Application Priority Data

Sep. 11, 1985 [GB] United Kingdom ............. 8522535

[51] Int. Cl.$^5$ .............. C07H 17/02; C07H 23/00; G01N 24/00; A61B 5/05
[52] U.S. Cl. .................. 536/7.3; 536/17.2; 536/17.4; 536/53; 536/121; 536/101; 536/102; 536/103; 536/112; 436/173; 128/653.2; 424/9
[58] Field of Search .............. 536/121, 101, 103, 112, 536/17.2, 17.3, 17.4, 17.9, 56, 102, 114; 436/173; 128/653.2; 424/9

[56] References Cited

U.S. PATENT DOCUMENTS 3,966,744 6/1976 Goldstein et al. .............. 546/22
3,966,764 6/1976 Goldstein et al. .............. 424/9

FOREIGN PATENT DOCUMENTS 1218597 3/1987 Canada .
1240679 8/1988 Canada .
71564 7/1982 European Pat. Off. .
85/05554 12/1985 PCT Int'l Appl. .

OTHER PUBLICATIONS

Keana, Newer Aspects of the Synthesis and Chemistry of Nitroxide Spin Labels, "Chemical Reviews", 78(1) 37–64 (1978).
Ehman et al., Diradical Nitroxyl Spin Label Contrast Agents for Magnetic Reasonance Imaging, A Comparison of Relaxation Effectiveness; "Investigative Radiology", 21 125–131 (Feb. 1986).
Brasch et al., (Jun. 1983) "Work in Progress: Nuclear Magnetic Resonance Study of a Paramagnetic Nitroxide Contrast Agent for Enhancement of Renal Structures in Experimental Animals, Radiology", 147: pp. 773–779.

Primary Examiner—Johnnie R. Brown
Assistant Examiner—Everett White
Attorney, Agent, or Firm—Wenderoth, Lind & Ponack

[57] ABSTRACT

A polysaccharide chemically joined to a nitroxyl spin label (NSL) compound has use for the preparation of an NMR diagnostic composition. An agent for modifying $H_2O$ relaxation times in NMR diagnosis may comprise a polysaccharide to which is chemically linked both an NSL compound and an organic complexing agent to which is complexed a paramagnetic metal ion, such as Gd(III) or Cu(II). Polysaccharides include dextran, starch and cellulose. The preferred NSL compound is 4-amino-2,2,6,6-tetramethylpiperidine-1-oxyl.

11 Claims, No Drawings

CONTRAST AGENT FOR NMR IMAGING

Nitroxyl spin label (NSL) compounds are stable free radicals having the general formula:

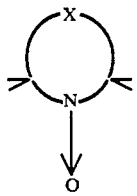

where X is a chain of two or three carbon atoms which may be substituted. NSL compounds have potential as paramagnetic agents for nuclear magnetic resonance (NMR) imaging because of a chemically stable unpaired electron. When NSL compounds are placed in a magnetic field, the electron aligns with the field; as a much stronger magnetic dipole than unpaired protons, the unpaired electron alters the local magnetic field experienced by protons around it, reducing $T_1$ and $T_2$ relaxation times.

Many different NSL compounds are available commercially; others can readily be synthesized using methods described in the literature. The potential of NSL compounds as contrast agents for NMR imaging is qualified by the fact that they are somewhat unstable in vivo. NSL compounds have been reported for the NMR imaging of kidneys (V. M. Runge (1983) Radiology 147 789) and tumors (R. L. Ehman (1985) 3 Magnetic Resonance Imaging). NSL compounds have been studied in vitro (J. D. Lovin (1985) Magnetic Resonance Imaging 3 73) and have been shown to be unstable to high concentrations of ascorbic acid being readily reduced to hydroxylamine (W. R. Couet (1984) Pharm. Res. 5 203).

NSL compounds have been used to label various compounds of biological interest. In particular two authors have reported the spin-labelling of polysaccharides. M. J. Adam et al (Carbohydrate Research (1979) 68, C17 to C20) used a triazine reagent but achieved only a limited degree of conjugation. T. P. Mawhinney et al (Carbohydrate Research (1983) 116, C1 to C4) used a carbanion reagent and achieved greater conjugation. But neither author suggests that the complexes might be useful as contrast agents for NMR imaging in vivo.

In one aspect, the present invention comprises the use of a polysaccharide-NSL complex for the preparation of an NMR diagnostic composition. In another aspect, it comprises the use of a polysaccharide-NSL complex as a contrast agent for NMR imaging.

The nature of the NSL compound is not critical to the invention. The NSL compound may be as described above. Our work has been primarily concerned with the compound-4 amino-2,2,6,6,-tetramethylpiperidine-1-oxyl (4-aminoTEMPO).

Various different polysaccharides, including chemical derivatives thereof, may be used, and will have an important influence on the properties of the complex. The polysaccharide may be water-soluble, such as dextran or dextrin, or water-insoluble, such as cellulose or sepharose or starch. Sepharose is a bead-formed gel prepared by cross-linking agarose. Other possible starches include amylose, xylan, mannan, locust-bean gum and guar gum. Compositions based on water-soluble polysaccharides may be administered orally or parenterally; compositions based on water-insoluble polysaccharides are mainly suitable for oral administration.

The polysaccharide may be metabolizable or non-metabolizable by the animal to which it is administered, or by its intestinal flora. Compounds which are not metabolized within the time span required for NMR scanning are regarded herein as non-metabolizable, even though they may be metabolized over a much longer time span. Cellulose, sepharose and dextran are non-metabolizable by humans, whereas starch and dextrin are metabolizable.

The polysaccharide-NSL complexes may be prepared by methods well described in the literature. The polysaccharide may first be activated, e.g. by means of chloroacetic acid or cyanogen bromide, followed by reaction with the NSL compound. Suitable reaction conditions are indicated in the examples below. In some of our studies chloroacetic acid has often proved a more effective activating agent than cyanogen bromide.

In another aspect, this invention provides an agent for modifying relaxation times in NMR diagnosis comprising a polysaccharide to which is chemically linked both an NSL compound and an organic complexant to which is complexed a paramagnetic metal ion.

Agents for modifying relaxation times in NMR diagnosis comprising a polysaccharide having chemically linked to it an organic complexant to which is complexed a paramagnetic metal ion, are described in International Patent Application PCT/GB85/00234 filed May 31, 1985. According to that specification, suitable paramagnetic metal ions are well known in the field and include those lanthanide elements with atomic numbers 58 to 70 and those of the transition metals with atomic numbers 21 to 29, 42 and 44. Preferred are Mn(II), Cu(II), Fe(II), Gd(III), Fe(III), Cr(III), Dy(III) and V(IV). Factors affecting the choice of metal ion are its paramagnetic properties, the stability of the metal ion-complexant-polysaccharide moiety, its toxicity, and the extent to which the metal ion in the complex interacts with water so as to vary the proton relaxation times.

The organic complexing agent may be one which forms a chelate with the chosen metal ion. Preferred are the aminopolyacetic acids such as Nitrilotriacetic acid N,N,N',N'-ethylenediamine tetraacetic acid (EDTA)

N-hydroxyethyl-N,N',N'-ethylenediamine triacetic acid

N,N,N',N",N"-diethylene triamine pentaacetic acid (DTPA)

N-hydroxyethylimino diacetic acid.

Particularly preferred are EDTA and DTPA.

The complexant may be chemically linked to the polysaccharide by known chemical methods for example by the use of cyanogen bromide. The possibility arises that a complexant directly linked to a polysaccharide may be sterically hindered from chelating the paramagnetic metal ion. This risk may be avoided by the use of a linker molecule between the complexant and the polysaccharide. The chemistry may be represented thus:

$$X-OH + BrCN \rightarrow X-OCN + HBr$$

$$X-OCN + H_2N-(CH_2)_n-NH_2 + H_2O \rightarrow X-OCO-NH-(CH_2)_n-NH_2 + NH_3$$

where X is the polysaccharide residue, and n is up to 10, for example from 4–8.

Then:

XOCO—NH—(CH$_2$)$_n$—NH$_2$+HOCO—Y→X-OCO—NH—(CH$_2$)$_n$—NHCO—Y+H$_2$O where Y is the complexant residue.

It is presently thought that the value of n is not critical, and indeed that the linker arm may not be needed at all in some cases. Where no linker is used, the complexant may be joined directly to the polysaccharide by known chemical techniques.

According to the present invention there is linked to the polysaccharide, not only the organic complexant-/paramagnetic metal ion, but also an NSL compound as described above. In order to prepare such agents, the polysaccharide may be first activated, e.g. by cyanogen bromide, followed by reaction together with the NSL compound and chemical linker arm. The organic complexant is subsequently joined to the end of the linker arm and finally used to complex the paramagnetic metal ion.

When the polysaccharide is insoluble, its physical state will depend on how it is to be administered. Finely divided material is preferably used; for example; 5 micron fibrous cellulosic material. This increases the specific surface area, and hence may increase the rate and extent of reaction with the NSL compound and (in some cases) with the complexant. It is this reaction that determines how much NSL compound (and in some cases how much paramagnetic metal ion) can be attached to unit weight of polysaccharide. Useful NMR contrast agents preferably contain at least one NSL molecule (and where appropriate at least one paramagnetic metal ion) per one hundred sugar units of the polysaccharide.

It is hoped that the polysaccharide-NSL contrast agents with which the present invention is concerned may have several advantages:

(a) NSL compounds are known to be somewhat unstable in vivo. Joining them to a polysaccharide matrix may increase their stability.

(b) If the nitroxyl free radical is reduced in vivo to hydroxylamine, it will still remain bound to the polysaccharide. Hence, binding to the polysaccharide reduces the toxicity.

(c) An NSL compound may have a greater effect on proton relaxation times when joined to a polysaccharide matrix than when in the free state. This advantage may be enhanced by joining the NSL compound to the polysaccharide via a linker arm, so as to give the NSL compound a greater degree of rotational freedom.

(d) The biodistribution of a polysaccharide-NSL compound will be different from that of the free NSL compound, and can be tailored in accordance with known criteria to provide useful diagnostic information.

(e) Contrast agents that include, not only an NSL compound, but also a paramagnetic metal ion joined to a polysaccharide matrix, have a unique combination of two different kinds of paramagnetic centers in the same molecule. This may be expected to generate more useful diagnostic information than could be obtained from a single kind of paramagnetic center.

The following examples illustrate the invention. Examples 1, 2 and 3 show respectively the binding of 4-aminoTEMPO to dextran, cellulose and starch, via activation of polysaccharides by chloroacetic acid or CNBr. Binding of 4-aminoTEMPO and 1, 6-diaminohexane to starch is shown in Example 3, with subsequent work up to a polymer containing two paramagnetic centers (NSL and gadolinium (III) ions).

EXAMPLE 1

DEXTRAN-NITROXYL DERIVATIVE

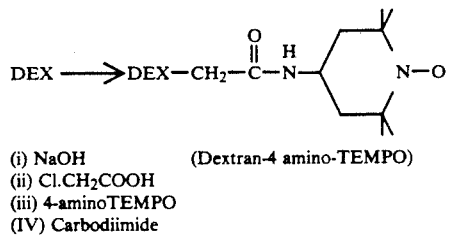

(i) NaOH  
(ii) Cl.CH$_2$COOH  
(iii) 4-aminoTEMPO  
(IV) Carbodiimide (Dextran-4 amino-TEMPO)

2 g dextran (18 k) was dissolved in 20 mls H$_2$O. 18 g NaOH in 50 mls H$_2$O was added to the dextran solution and the reaction mixture stirred for 20 minutes. 26 g chloroacetic acid was then added, the solution stirred for 5 hrs, then a further 26 g chloroacetic acid was added. The solution was stirred for 10 hrs., and the sample rotary evaporated to approximately 20 mls and then dialyzed over 24 hrs. (5×3 liter H$_2$O changes). The aqueous solution of carboxy dextran was then rotary evaporated to dryness and taken up in 20 mls H$_2$O. The pH was adjusted to pH7 by 2M NaOH addition. 0.3 g 4-aminoTEMPO was added slowly the pH maintained at pH6, and 0.6 g carbodiimide (1-(3-dimethyl aminopropyl)-3-ethyl carbodiimide hydrochloride) was then added. After 2 hrs. stirring a further 0.3 g 4-aminoTEMPO and 0.6 g carbodiimide were added, and the reaction mixture stirred at pH6 for 12 hrs., and then dialyzed over 24 hrs. (3×3 liter H$_2$O changes). The final dialyzed solution of dextran-4-aminoTEMPO was then freeze dried and kept aside for electron spin resonance (ESR) studies and NMR T$_1$ relaxation measurements of aqueous solutions of dextran-4-aminoTEMPO.

ESR

Studies showed nitroxyl (4-aminoTEMPO) binding. The exact number of nitroxyls bound per g dextran could not be determined. Estimated substitution was one 4-aminoTEMPO molecule per 50 glucose units.

NMR

H$_2$O T$_1$ values were recorded for aqueous dextran-4-aminoTEMPO solutions at 200 MHz using 90% H$_2$O 10% D$_2$O under various conditions. The results were as follows

| Dextran-4-aminoTEMPO conc (g/ml) | Dextran MWT | Activating Agent | T$_1$ value (ms) at Temperature | |
|---|---|---|---|---|
| | | | 27° C. | 37° C. |
| 0.07 | 18 k | CNBr | 1571 | |
| 0.07 | 18 k | chloroacetic acid | 580 | |
| 0.07 | 82 k | CNBr | 1500 | |
| 0.035 | 150 k | chloroacetic acid | 404 | 503.4 |
| 0.07 | 150 k | chloroacetic acid | 186.4 | 215.1 |
| 0.134 Dextran | 18 k | — | 3300 | |
| H$_2$O | — | — | 3400 | |

The T$_1$ value of 0.07 g/ml of dextran-4-aminoTEMPO (150 k) is equivalent to the T$_1$ value of 38 mM free 4-aminoTEMPO.

The change with time of the ESR spectra for aqueous solutions of free 4-aminoTEMPO and 4-aminoTEMPO bound (by CNBr activation) to dextran (18K) in the presence of ascorbic acid was studied. Into each of sample A (4-aminoTEMPO, concentration 0.42 mM) and sample B (dextran-4-aminoTEMPO, concentration 0.017 g/ml) was mixed ascorbic acid to give an ascorbic acid concentration of 1.04 mM. At a point 2½ minutes after the ascorbic acid addition, the ESR spectrum for sample A indicated that almost 100% nitroxide reduction had occurred. Sample B, at 2½ minutes after the ascorbic acid addition, was found to have undergone about 75% nitroxide reduction and at 15 minutes after the ascorbic acid addition was found to have undergone about 90% nitroxide reduction, according to the ESR spectrum of the sample. These results show the increased stability of the dextran-bound 4-aminoTEMPO compared to the unbound compound. Similar experiments performed to determine the effect of plasma (lyophilized human plasma prepared prior to usage) on the E.S.R. spectra of aqueous solutions of free and dextran-bound 4-aminoTEMPO confirmed that the bound 4-aminoTEMPO was more stable to reduction than the free compound.

Further confirmation of the increased stability of the dextran-bound 4-aminoTEMPO was provided by a study of the change in the $H_2O$ $T_1$ relaxation times of aqueous solutions of 4-aminoTEMPO and of dextran-4-aminoTEMPO to each of which had be added ascorbic acid and, in a separate study, plasma.

EXAMPLE 2

CELLULOSE-NITROXYL DERIVATIVE

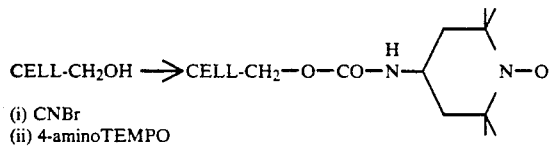

(i) CNBr
(ii) 4-aminoTEMPO 4 g cellulose was dispersed in 100 mls $H_2O$ (pH 7) and 1 ml 1M NaOH added (pH 11). Then 2 g CNBr was added slowly, the solution was stirred vigorously, and a pH of 10.5 maintained for 20 minutes by 2M NaOH addition. After 20 minutes 2M HCl was added until pH 7 was recorded for the solution. 0.4 g 4-aminoTEMPO was added, and the mixture left standing overnight at pH 7. The cellulose-nitroxyl derivative (cellulose-4-aminoTEMPO) was then washed by filtration (1 liters $H_2O$) to remove any excess free radical 4-aminoTEMPO. The product was then oven dried at 75° C. for two days. Electron spin resonance studies performed on the solid compound, and a $T_1$ measurement of an aqueous suspension of cellulose-4-aminoTEMPO were recorded.

ESR studies showed nitroxyl binding. The exact substitution ratio could not be determined but was estimated at one 4-aminoTEMPO molecule per 50 glucose units.

NMR studies showed the $H_2O$ $T_1$ value of an aqueous suspension of the complex (0.12 g/ml) to be 2448 ms compared to a cellulose suspension (0.12 g/ml) having an $H_2O$ $T_1$ value of 3300 ms, thus demonstrating that the bound NSL was an effective proton relaxation agent.

However ESR and $T_1$ NMR relaxation measurements of a cellulose-4 aminoTEMPO derivative formed via chloracetic acid activation (of Example 1) showed a greater uptake of 4-aminoTEMPO onto the polymer backbone.

The $H_2O$ $T_1$ value of aqueous suspension of the complex (0.04 g/ml slurry) was 646 ms.

ESR studies showed approximately one 4-aminoTEMPO molecule bound per 30 glucose units. This confirms data obtained for dextran-4-aminoTEMPO synthesis in that a greater uptake of 4-aminoTEMPO onto the polysaccharide polymer is achieved via chloroacetic acid activation of the polymer.

EXAMPLE 3

STARCH—LINKER—DTPA—Gd(III) DERIVATIVE
|
NITROXYL i.e. 2 paramagnetic centers Gd(III) and NSL (4-aminoTEMPO).

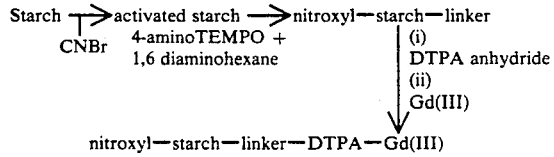

(1) 6 g starch was dispersed in 300 mls $H_2O$ and 2 mls 2M NaOH was added. A pH of 11 was recorded.

(2) 2.2 g CNBr/7 mls DMF was added slowly over 5 minutes. The pH rapidly fell, and was kept at pH 10 for 20 minutes by 2M NaOH addition.

(3) After 20 minutes the pH was allowed to fall to pH 7 1.1 g 4-aminoTEMPO/5 mls $H_2O$ and 1.2 g 1,6-diaminohexane/15 mls $H_2O$ were added individually in 0.5 ml portions alternately. pH7 was maintained by HCl and NaOH additions. The mixture was stirred at room temperature for 12 hrs. Then the product (nitroxyl-starch-linker) was washed by filtration (1 liter $H_2O$ wash). A small portion was kept aside for electron spin resonance studies and $H_2O$ $T_1$ relaxation measurement.

(4) The rest of product from stage 3 was stirred in 50 mls $NaHCO_3$ buffer (0.1M; pH8). 1 g DTPA anhydride was added, after 10 minutes the pH fell to pH 5. The reaction mixture was stirred for 3 hrs, then washed by filtration with 1 liter $H_2O$. A small portion of product (nitroxyl-starch-linker-DTPA) was kept aside for ESR and $H_2O$ $T_1$ measurement studies.

(5) To 2 g nitroxyl-starch-linker-DTPA from 4), 0.2 g $Gd(NO_3)_3 \cdot 5H_2O$ in 40 mls $H_2O$ was added. The reaction mixture was stirred for 6 hrs, then washed by filtration with 1 liter $H_2O$. ESR and $H_2O$ $T_1$ data were recorded for the product nitroxyl-starch-linker-DTPA-Gd(III).

NMR $H_2O$ $T_1$ data are presented below for 0.12 g/ml aqueous suspension, for the series of products. $T_1$ was recorded at 27° C. at 200 MHz. The figures are compared to that for starch-nitroxyl alone (prepared as cellulose-nitroxyl derivative as in Example 2).

| Sample (0.12 g/ml $H_2O$ (10% $D_2O$) | $T_1$/ms |
|---|---|
| starch-nitroxyl (via CNBr activation) | 1980 |
| nitroxyl-starch-linker | 2070 |
| nitroxyl-starch-linker-DTPA | 2170 |
| nitroxyl-starch-linker-DTPA-Gd(III) | 540.7 |
| Starch | 3300 |

ESR

Electron spin resonance studies showed the binding of 4-aminoTEMPO to starch, and subsequent binding of Gd(III) ions to DTPA attached to the starch backbone via a linker arm.

EXAMPLE 4

By methods analagous to that described in Example 3, were prepared the following Cu(II) derivatives:
(i) nitroxyl-cellulose-linker-DTPA-Cu(II) and
(ii) nitroxyl-starch-linker-DTPA-Cu(II).
(N.B. the linker compound used being 1,6-diaminohexane)

$H_2O$ $T_1$ measurement studied were carried out on the derivatives (i) and (ii) above, as solutions in agar (15% solution: 10% $D_2O$) at 200 MHz at 27° C. The results are shown in the table below.

| Sample | concentration (g/ml) | $T_1$ (ms) |
|---|---|---|
| cellulose-nitroxyl (via CNBr activation) | 0.0221 | 1246 |
| nitroxyl-cellulose-linker-DTPA | 0.022 | 1352 |
| nitroxyl-cellulose-linker-DTPA-Cu(II) | 0.022 | 1104 |
| starch-nitroxyl (via CNBr activation) | 0.022 | 2000 |
| nitroxyl-starch-linker-DTPA | 0.0201 | 3020 |
| nitroxyl-starch-linker-DTPA-Cu(II) | 0.200 | 2160 |
| agar | | 3358 |

The stability against nitroxyl reduction by ascorbic acid was studied by analyses of the changes in the ESR spectra for the derivatives
(A) starch-nitroxyl; and
(B) nitroxyl-starch-linker-DTPA-Cu(II), in the presence of ascorbic acid After 5 minutes, starting from the addition to 0.6 g of each of samples (A) and (B) of 12.5 mM of ascorbic acid, the % nitroxide reductions were determined as 67% for sample (A) and 61.5% for sample (B). After 10 minutes from the ascorbate addition, the % nitroxide reductions were 72% for sample A and 64% for sample (B). These results show the additional stability against reduction provided by the presence of Cu(II) in the species.

EXAMPLE 5

Doses of 0.1 ml of 0.1 g/ml of dextran-4-aminoTEMPO were injected into rats and urine samples were collected 24 hours after injection and analysed. Analysis of the urine samples showed that 4-aminoTEMPO bound to 18 k and to 60 k dextran were excreted but that there was no excretion of 4-aminoTEMPO bound to 150 k dextran, that all excreted nitroxyl-containing compound was still in a bound form (to the dextran polymer) and that approximately 60% nitroxide reduction had occurred.

Excretion studies were also performed using administered doses of 0.1 g of starch-nitroxyl. In all cases, the excreted nitroxyl (after 24 hours) was still bound to the polymer. 39% of the excreted material had been reduced.

EXAMPLE 6

To demonstrate the contrast enhancement in vivo of the materials of the present invention, experiments were conducted in which rabbits, to which had been administered a polysaccharide-bound NSL, were subjected to NMR imaging.

To rabbits (body weight—4 to 5 kg) under anaesthesia was administered orally, in a dosage of 1 g in 20 ml physiological saline solution, starch-nitroxyl (i.e. 4-aminoTEMPO bound to starch). 20 minutes after the administration of the dose, proton NMR images of the stomach/upper gut regions showed areas of contrast due to the shortening of the proton relaxation times in selected regions. The signals were stable over ½ hour showing that no substantial reduction of the nitroxyl group had occurred in the bowel over that time.

In a similar fashion, nitroxyl-starch-linker-DTPA-Cu(II) (see Example 4) was administered to rabbits in a dosage of 1 g in 10 ml physiological saline solution. Again, after 20 minutes from administration, proton NMR images of the stomach/upper gut regions showed good areas of contrast but of greater contrast that had been observed with the starch-nitroxyl administration described above.

In a separate imaging study, rabbits prepared in a manner similar to that above were injected intravenously with dextran-4-aminoTEMPO (using 18 k dextran). The dose was 0.1 g in a 1 ml shot. 40 minutes after the administration, proton NMR images of the kidney showed good contrast in the medulla.

We claim:

1. An NMR diagnostic agent comprising a polysaccharide selected from the group consisting of dextran, dextrin, cellulose, Sepharose and starch, to which are chemically linked by a cyanogen bromide linkage both a nitroxyl spin label compound and an organic complexant consisting of an aminopolyacetic acid to which is complexed a paramagnetic metal ion having an atomic number selected from the group consisting of 58 to 70, 42, 44 and 21 to 29, wherein the organic complexant forms a chelate with the said paramagnetic metal ion.

2. The agent as claimed in claim 1 wherein the nitroxyl spin label compound is 4-amino-2, 2,6,6-tetramethylpiperidine-1-oxyl.

3. The agent as claimed in claim 1, wherein the organic complexant is diethylenetriamine pentaacetic acid.

4. The agent as claimed in claim 1, wherein the paramagnetic metal ion is gadolinium (III).

5. The agent as claimed in claim 1, wherein the paramagnetic metal ion is copper (II).

6. The agent as claimed in claim 1 wherein the aminopolyacetic acid is selected from the group consisting of nitrilotriacetic acid, N,N,N',N'-ethylene diamine-tetraacetic acid, N-hydroxyethyl-N,N',N'-ethylene diamine triacetic acid, N,N,N',N'',N''-diethylene triamine pentaacetic acid and N-hydroxyethylimino diacetic acid.

7. An NMR diagnostic agent comprising a polysaccharide selected from the group consisting of dextran, dextrin, starch, cellulose and sepharose to which is chemically linked by a cyanogen bromide linkage both a nitroxyl spin label compound and an organic complexant consisting of an aminopolyacetic acid to which is complexed a paramagnetic metal ion having an atomic number selected from the group consisting of 58 to 70, 42, 44 and 21 to 29, wherein the organic complexant forms a chelate with the said paramagnetic metal ion.

8. An NMR diagnostic agent comprising a polysaccharide selected from the group consisting of dextran, dextrin, starch, cellulose and sepharose to which is chemically linked by a cyanogen bromide linkage both a nitroxyl spin label compound and an organic complexant consisting of an aminopolyacetic acid selected from the group consisting of nitrilotriacetic acid, N,N,N',N'-ethylene diamine tetraacetic acid, N-hydroxyethyl-N,N',N'-ethylene diamine triacetic acid, N,N,N',N'',N''-diethylene triamine pentaacetic acid and N-hydroxy-ethylimino diacetic acid to which is complexed a paramagnetic metal ion having an atomic number selected from the group consisting of 58 to 70, 42, 44 and 21 to 29.

9. An NMR diagnostic agent consisting of starch to which is chemically linked by a cyanogen bromide linkage a nitroxyl spin label compound consisting of 4-amino-2,2,6,6,-tetramethylpiperidine-1-oxyl and diethylene triamine pentaacetic acid to which is complexed gadolinium (III).

10. An NMR diagnostic agent consisting of cellulose to which is chemically linked by a cyanogen bromide linkage a nitroxyl spin label compound consisting of 4-amino-2,2,6,6, -tetramethylpiperidine-1-oxyl and diethylene triamine pentaacetic acid to which is complexed copper (II).

11. An NMR diagnostic agent consisting of starch to which is chemically linked by a cyanogen bromide linkage a nitroxyl spin label compound consisting of 4-amino-2,2,6,6,-tetramethylpiperidine-1-oxyl and diethylene triamine pentaacetic acid to which is complexed copper (II).

* * * * *